(12) United States Patent
Zambriski et al.

(10) Patent No.: US 10,420,387 B2
(45) Date of Patent: Sep. 24, 2019

(54) EXERCISE PERFORMANCE MONITORING APPARATUS

(71) Applicants: Sharon Ann Zambriski, Cedar Park, TX (US); Nicholas Andrew Cooper, Cedar Park, TX (US); Max William Cooper, Cedar Park, TX (US); Andrew Burton Cooper, Cedar Park, TX (US)

(72) Inventors: Sharon Ann Zambriski, Cedar Park, TX (US); Nicholas Andrew Cooper, Cedar Park, TX (US); Max William Cooper, Cedar Park, TX (US); Andrew Burton Cooper, Cedar Park, TX (US)

(*) Notice: Subject to any disclaimer, the term of this patent is extended or adjusted under 35 U.S.C. 154(b) by 147 days.

(21) Appl. No.: 15/721,646

(22) Filed: Sep. 29, 2017

(65) Prior Publication Data

US 2019/0099123 A1    Apr. 4, 2019

(51) Int. Cl.
| | | |
|---|---|---|
| *A43B 3/00* | (2006.01) | |
| *A43B 5/00* | (2006.01) | |
| *G01L 5/00* | (2006.01) | |
| *A41D 19/00* | (2006.01) | |

(Continued)

(52) U.S. Cl.
CPC .......... *A43B 3/0005* (2013.01); *A61B 5/0024* (2013.01); *A61B 5/1036* (2013.01); *A61B 5/6806* (2013.01); *A61B 5/6807* (2013.01); *A61B 5/7445* (2013.01); *A41D 19/0027* (2013.01); *A43B 5/00* (2013.01); *A61B 2562/0247* (2013.01); *A61B 2562/046* (2013.01); *A61B 2562/166* (2013.01); *A63B 2220/56* (2013.01)

(58) Field of Classification Search
CPC .............. A43B 3/0005; A63B 24/0003; A63B 2220/56; A41D 19/0027
See application file for complete search history.

(56) References Cited

U.S. PATENT DOCUMENTS

| | | |
|---|---|---|
| 6,216,545 B1 | 4/2001 | Taylor |
| 9,301,563 B2 | 4/2016 | Hardy et al. |
| 9,462,844 B2 | 10/2016 | Schrock et al. |

(Continued)

*Primary Examiner* — Daniel J Colilla

(57) ABSTRACT

The exercise performance monitoring apparatus consists of gloves and shoes that have embedded pressure sensor arrays to measure pressure applied to them during exercise. The gloves and shoes send the pressure data using wireless RF transmitters to a central display control unit located on each glove. The gloves have color LED strips which change color depending on whether the gloves or shoes are measuring equal pressures. The glove displays the state of balance between the glove and shoe pressures using separate LED displays on each glove. The pressure balance is adjustable as well as the selection of colors to display. The user can at a glance see if he or she is in balance when performing the specific exercise by observing the color shown on the glove display. The glove display for either glove or shoe pressure will flash the color representing unbalanced pressures if the pressures are unbalanced on the glove having the highest or lowest pressure depending on user preference. A steady color is shown when the pressure is balanced and then changes color as soon as the pressures become unbalanced. A wireless enabled device such as a smart phone can also be used to monitor the exercise in lieu of using the glove LED display.

22 Claims, 10 Drawing Sheets

(51) Int. Cl.
*A61B 5/00* (2006.01)
*A61B 5/103* (2006.01)

(56) References Cited

U.S. PATENT DOCUMENTS

| | | |
|---|---|---|
| 2007/0129907 A1 | 6/2007 | Demon |
| 2012/0212505 A1* | 8/2012 | Burroughs .......... G06F 19/3481 |
| | | 345/629 |
| 2015/0177081 A1 | 6/2015 | Steier |
| 2016/0067584 A1 | 3/2016 | Giedwoyn et al. |
| 2016/0166178 A1 | 6/2016 | Fuss et al. |
| 2016/0299021 A1 | 10/2016 | Thillainadarrajah et al. |
| 2016/0375308 A1* | 12/2016 | Anderson .......... A63B 24/0087 |
| | | 482/5 |
| 2017/0197115 A1* | 7/2017 | Cook .................... A63B 26/003 |
| 2017/0319937 A1* | 11/2017 | Nevell ................ A63B 69/3608 |
| 2018/0333079 A1* | 11/2018 | Szekely ............... A61B 5/6806 |

\* cited by examiner

EXERCISE PERFORMANCE MONITORING APPARATUS

FIELD OF THE INVENTION

The present invention relates to the field of wearable exercise performance monitoring equipment and more particularly to wearable exercise apparel that have embedded sensors to monitor performance during exercise.

BACKGROUND OF THE INVENTION

There are a variety of wearable exercise performance monitoring devices available today to help monitor exercise performance. These are typically sold as fitness trackers and are typically devices that you wear on your wrist or strap around your chest. Some examples are wearable monitors that can monitor heart rate and have GPS tracking to allow other measurements such as tracking number of steps or distance. More recently, fitness tracking technology has extended into footwear including socks and sneakers. One product example is Sensoria® Smart Socks which are socks infused with 100% textile pressure sensors to inform you in real-time on your running technique. The smart garment connects to a light weight anklet which wirelessly relays data to the Sensoria. Fitness mobile app.

Another example in the form of a fitness tracking sneaker is Speed Form® Gemini 3 RE, SpeedForm® Velociti RE, and SpeedForm® Europa. RE available from tinder Armour. These shoes have a built-in sensor chip that connects to the UA MapMyRun app to track running data such as distance, speed, stride length, and even fatigue. There are also motion sensing products now available where motion sensors are attached to wearable items such as golf gloves in order to measure hand speed. Another example is sensors embedded in tennis wristbands that can track a player's racket velocity, height of the shot, and trajectory.

However, there are no wearable exercise monitoring products in the prior art that can be used to monitor exercises involving measuring balance such as weight lifting, yoga, gymnastics or body weight exercises. For example, yoga exercise is commonly done in a group where the instructor leads a variety of exercises involving balancing the pressure between hands and feet in a variety of body positions and postures. Indeed it would be desirable for people performing yoga to know if they are applying equal pressure to their hands or feet when exercising. Such feedback would be desirable to helping adjust their body positions to more evenly distribute pressure between the hands and feet.

BRIEF SUMMARY OF THE INVENTION

The invention provides a pair of pressure sensing gloves and pressure sensing shoes that collectively measure pressure points on both hands and feet. The gloves and shoes have an array of individual pressure sensors which measure pressure and convert the applied pressure to a voltage which is sent to an embedded electronic module mounted in each glove and shoe. Each embedded electronic module contains a microprocessor for calculating pressure statistics and a wireless transmitter to send the data to a wireless receiver located in each glove. Each glove contains a second embedded electronic module containing the wireless receiver and a microprocessor with an algorithm to compare the data sent by each glove and shoe pair. The algorithm compares the glove pressure data and shoe pressure data and determines whether the glove pressures are balanced and whether the shoes pressures are balanced.

If the glove pressures are balanced then the module sends a specific color command to two LED displays on each glove. For example if the glove pressures are in balance then both gloves might display green while this condition is met. An unbalanced glove pressure result would display a different color for example red. One glove LED display runs across adjacent to the knuckles of the hand on the side opposite of the palm and a second smaller LED display is located on the thumb on the palm side. This allows the user to monitor his glove balance no matter what orientation his hands are in during exercise.

A separate LED display wraps completely around the entire glove at the wrist end of the glove and is used to show the balance condition between the shoe pressures during exercise. If the shoe pressures are balanced then the module sends a specific color command to the shoe LED display on each glove. For example if the shoe pressures are in balance then both shoe LEDs might display green while this condition is met. An unbalanced shoe pressure result would display a different color for example red. When either the glove or shoe pressures are in an unbalanced state, additional information is indicated by using a flashing LED light on either the glove or shoe LED display that has the highest pressure of the two. The glove or shoe LED display on the side that has the lowest pressure would stay lit red until the pressure balance condition changes. As an alternative option to using the glove LED displays, a wireless enabled device such as a smart phone may be used to display the performance results of the glove or the shoes or both depending on user preference.

DETAILED DESCRIPTION OF THE INVENTION

Figure 1:
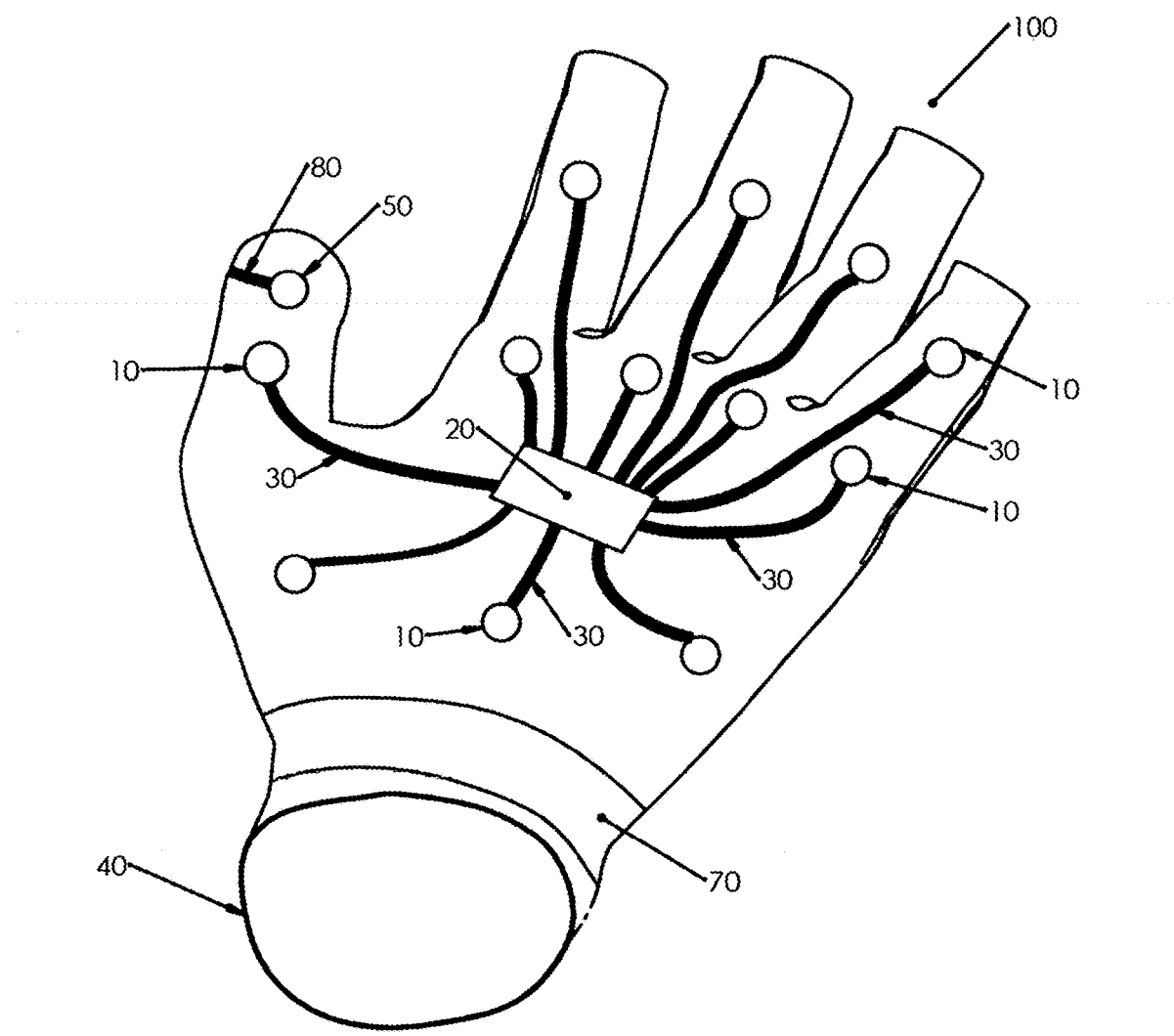
FIG. 1 is a perspective view of the pressure sensing glove with palm side facing up.

Referring now to the drawings and in particular FIG. 1, the pressure sensing glove of the present invention is designated by reference numeral 100. Although only the left hand glove is shown, the right hand glove would have the same components arranged in the same locations in a symmetric arrangement. Each glove 100 contains a plurality of pressure sensing elements 10 that are located at desirable locations on the hand where pressure is exerted during exercise such as near the finger tips, along the base of the fingers and along the bottom of the palm. The pressure sensing elements can be made from any type of electromechanical pressure sensors such as thin film capacitive sensors. Each pressure sensing element converts the pressure applied to it to an electrical signal which is transmitted via wire 30 to a primary electronic module 20. The glove housing 40 may be made of a variety of materials such as polyester/nylon blends, leather or neoprene foam rubbers. An LED display 70 is located at the wrist end of the glove and the display wraps completely around the glove so it can be visible at any angle. This LED display shows the balance condition being monitored on the pressure sensing shoes 200 during exercise. An LED display 50 is located near the distal end of the thumb and is intended to show the balance condition being monitored on the pressure sensing gloves during exercise. Wire 80 connects the LED display 50 to a secondary electronic module 90.

Figure 2:
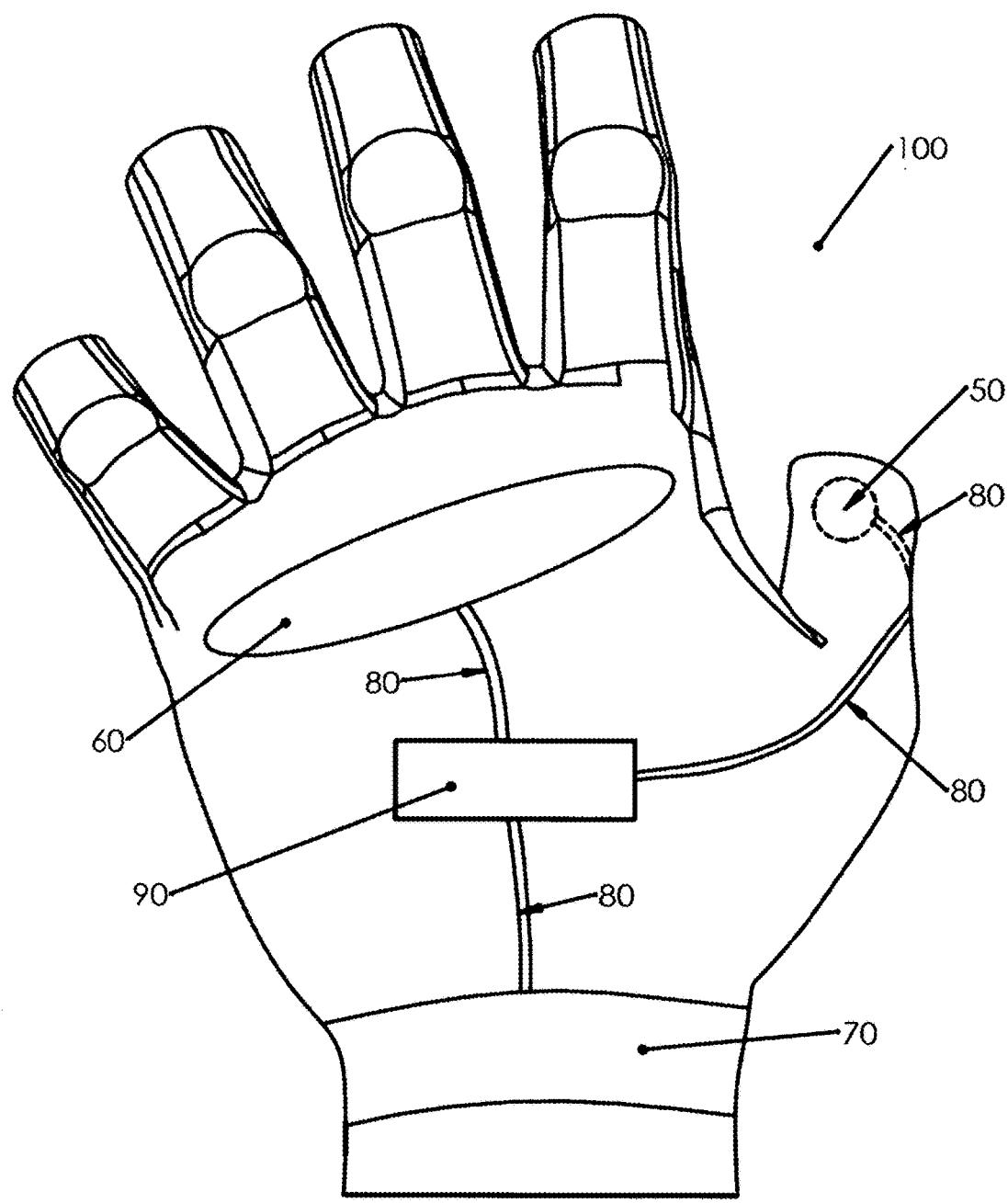
FIG. 2 is a perspective view of the pressure sensing glove with palm side facing down.

Referring next to FIG. 2, the top view of the pressure sensing glove 100 is shown. A secondary electronic module 90 is located near the center of the glove and transmits signals to three separate color LED displays 50, 60, and 70 via connecting wires 80. Each LED display shows a color depending on the state of the exercise and the actual color displayed for an exercise status may be changed by the user. The LED display 60 is preferably located along the base of the fingers adjacent to the knuckles of the hand and will light up in a specific color (for example red) when the left and right hand pressures are not the same (i.e. unbalanced) and will light up in a different color (for example green) when the left and right hand pressures are the same (i.e. balanced). An LED display 50 is located on the thumb on the palm side of the glove as shown and also will display the same color as LED display 60 for the specific balance state of the pressure sensing gloves. Having two separate LED displays 50 and 60 allows the user to see the state of balance between the pressure sensing gloves at any hand position during exercise. This allows for use of the exercise performance monitoring apparatus in a wide variety of sports such as weight lifting, yoga, gymnastics or body weight exercises.

Referring again to FIG. 2, by using a wireless enabled device and app, the electronic module 90 can be programmed to display specific colors desired by the user to represent balanced and unbalanced conditions for the pressure sensing gloves and shoes. The user may also select for unbalanced pressure conditions whether the highest or lowest pressure side is indicated by a flashing LED. The LED display 70 is located along the base of the glove near the wrist and is completely wrapped around the glove to be visible at all angles during exercise. LED display 70 is intended to display an exercise condition corresponding to the state of pressure balance between the left and right pressure sensing shoes 200. The LED display 70 will light up in a specific color (for example red) when the left and right shoe pressures are not the same or unbalanced and will light up in a different color (for example green) when the left and right hand pressures are the same or balanced.

Figure 3:
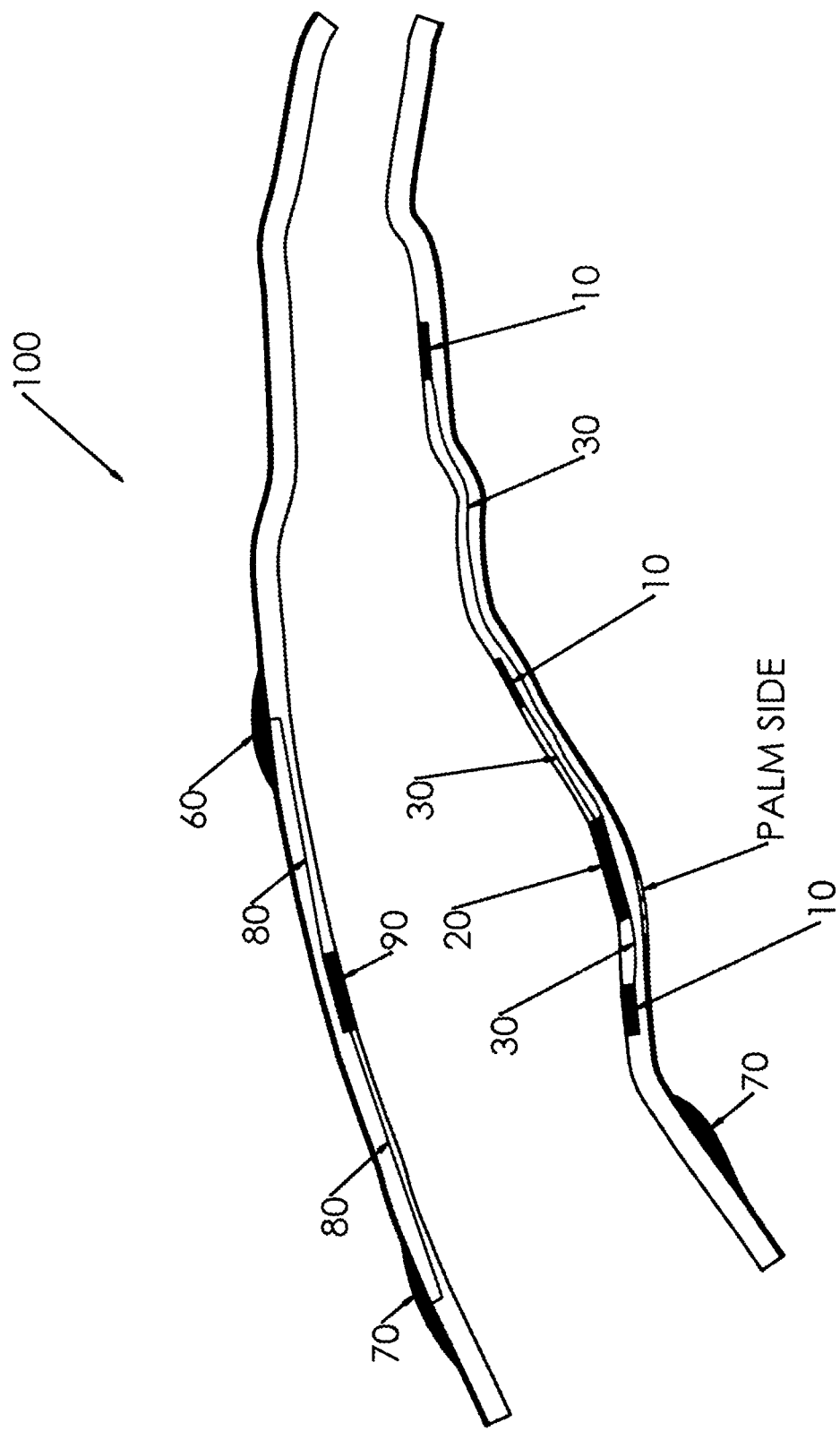
FIG. 3 is a cross section view of the pressure sensing glove.

Referring next to FIG. 3, a cross section view of the pressure sensing glove 100 is shown. Only LED displays 50, 60, and 70 are located at the outer surface of the glove. The connecting wiring 80 between LED displays and the secondary electronic module 90 are preferably embedded inside the glove housing 40 as shown. The pressure sensors 10 and the primary electronic module 20 are preferably located along the inner surface of the glove, and the connecting wiring 30 between the sensors and the primary electronic module are preferably embedded inside the glove housing so that they are not exposed to the outer surface. The glove housing 40 is several millimeters in thickness in order to contain all of the sensors, wiring, electronic modules and LED displays.

Figure 4:
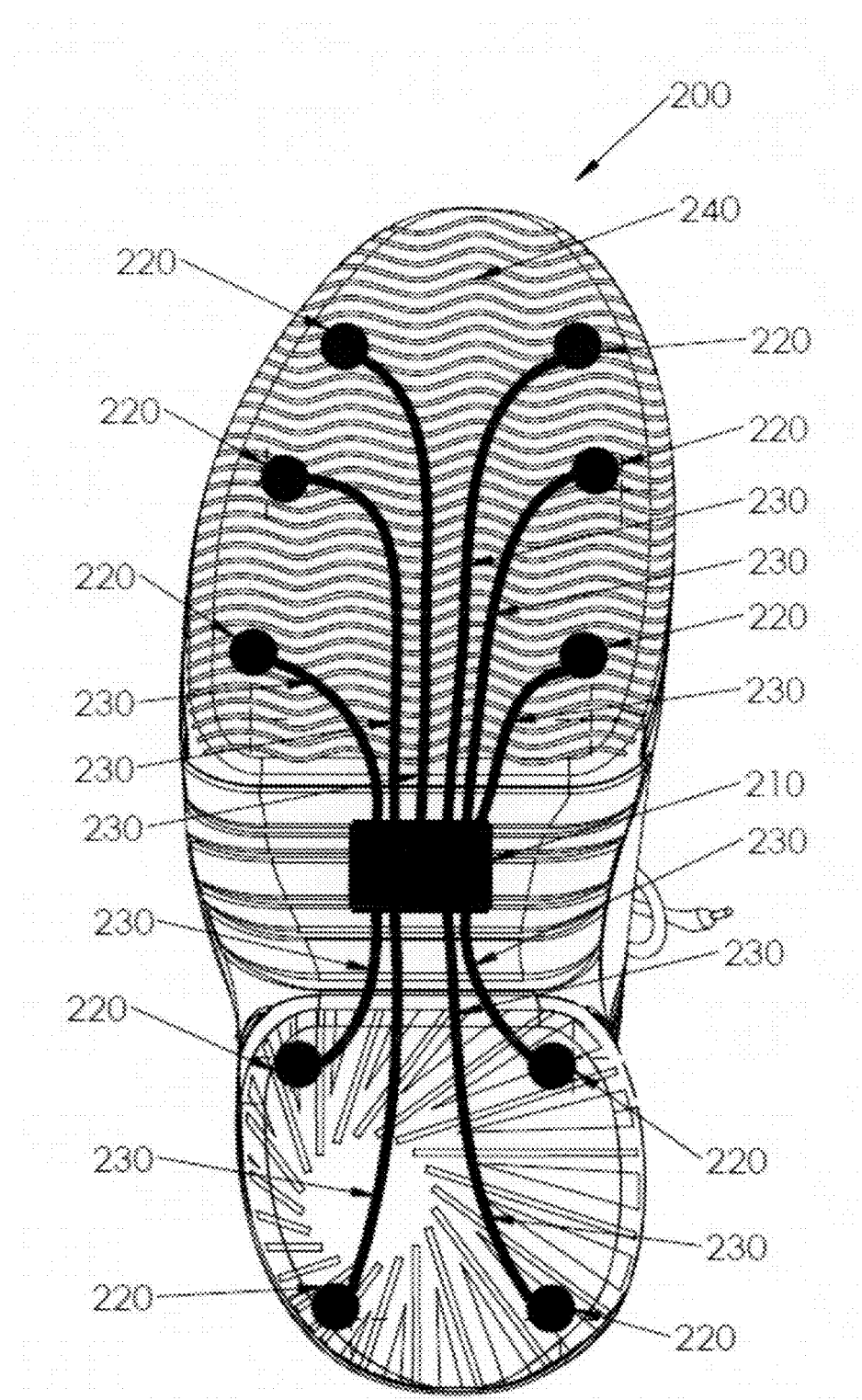
FIG. 4 is a bottom view of the pressure sensing shoe.

Referring next to FIG. 4, the pressure sensing shoe 200 is shown. The pressure sensing shoe is intended to be used during exercise just like any normal type of athletic footwear such as sneakers. Embedded within the insole of the shoe are a plurality of pressure sensing elements 220 that are located at desirable contact points where the foot can apply pressure. In the embodiment shown, there are ten pressure sensors 220 located around the perimeter of the shoe. The actual locations of the pressure sensing elements 220 could vary depending on which type of athletic shoe is used. For example running shoes and tennis shoes would be expected to have different pressure sensor locations since the applied pressure points playing tennis and running are different. Therefore the actual number of pressure sensor elements 220 and their actual locations in the shoe will vary depending on the specific style of athletic footwear selected.

Referring again to FIG. 4, the pressure sensor 220 is an electromechanical pressure sensor such as a thin film capacitive sensor. Each pressure sensor 220 converts the mechanical pressure applied to it to an electrical signal which is carried via wire 230 to a shoe mounted electronic module 210. The shoe housing 240 is preferably made of typical athletic footwear materials of construction such as leather and rubber. polyester/nylon blends, leather or neoprene foam rubbers.

Figure 5:
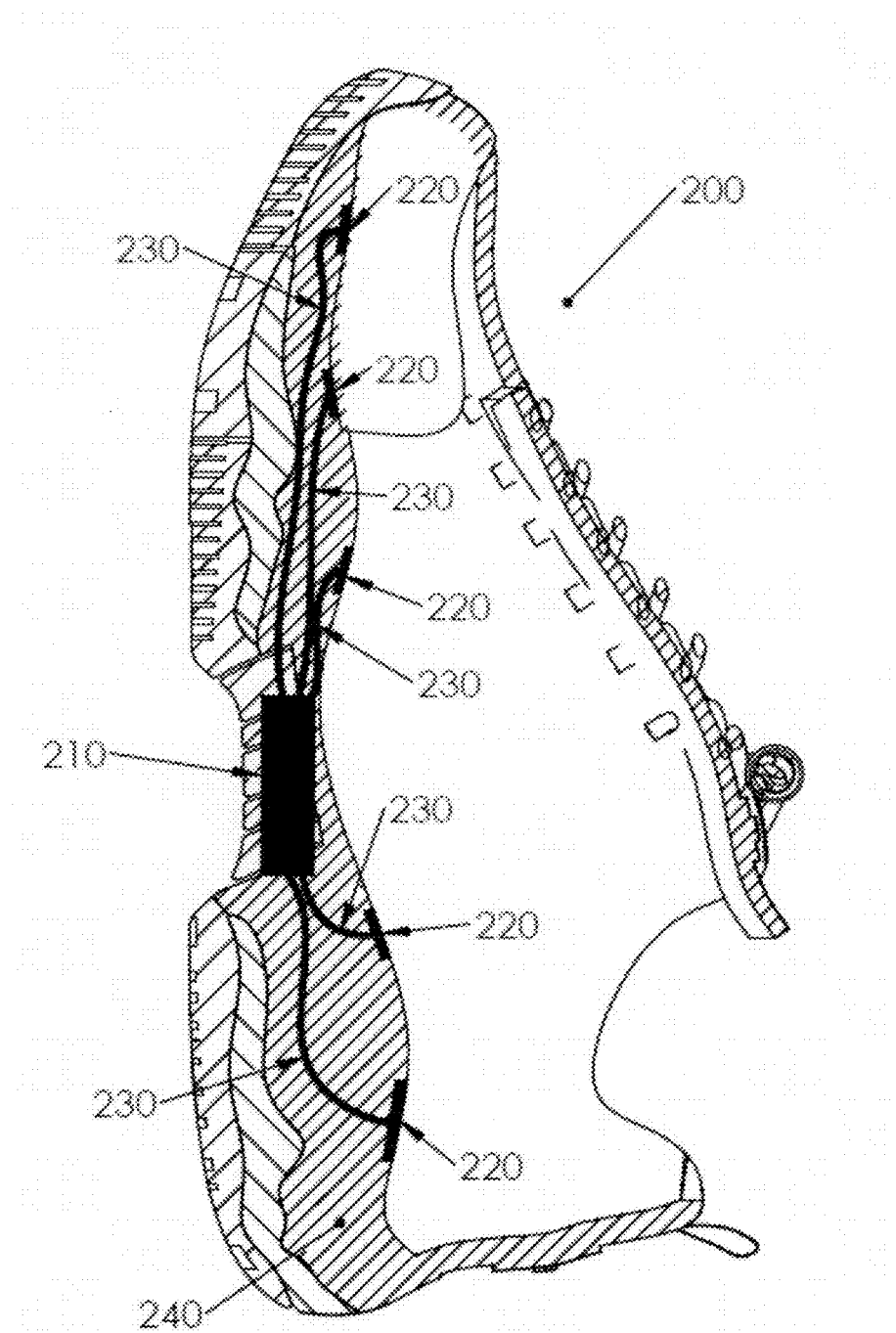
FIG. 5 is a cross section view of the pressure sensing shoe.

Referring next to FIG. 5, the pressure sensing shoe 200 is shown in cross section to include the preferred locations of the pressure sensors 220, the connecting wiring 230 and the shoe electronic module 210. In the preferred embodiment, these components are preferably embedded in the insole component of the shoe so that they are protected from exposure to outside elements. If a pressure sensing shoe 200 no longer works (for example from a dead battery or sensor), the insole can be replaced with a new insole to resume pressure monitoring.

Figure 6:
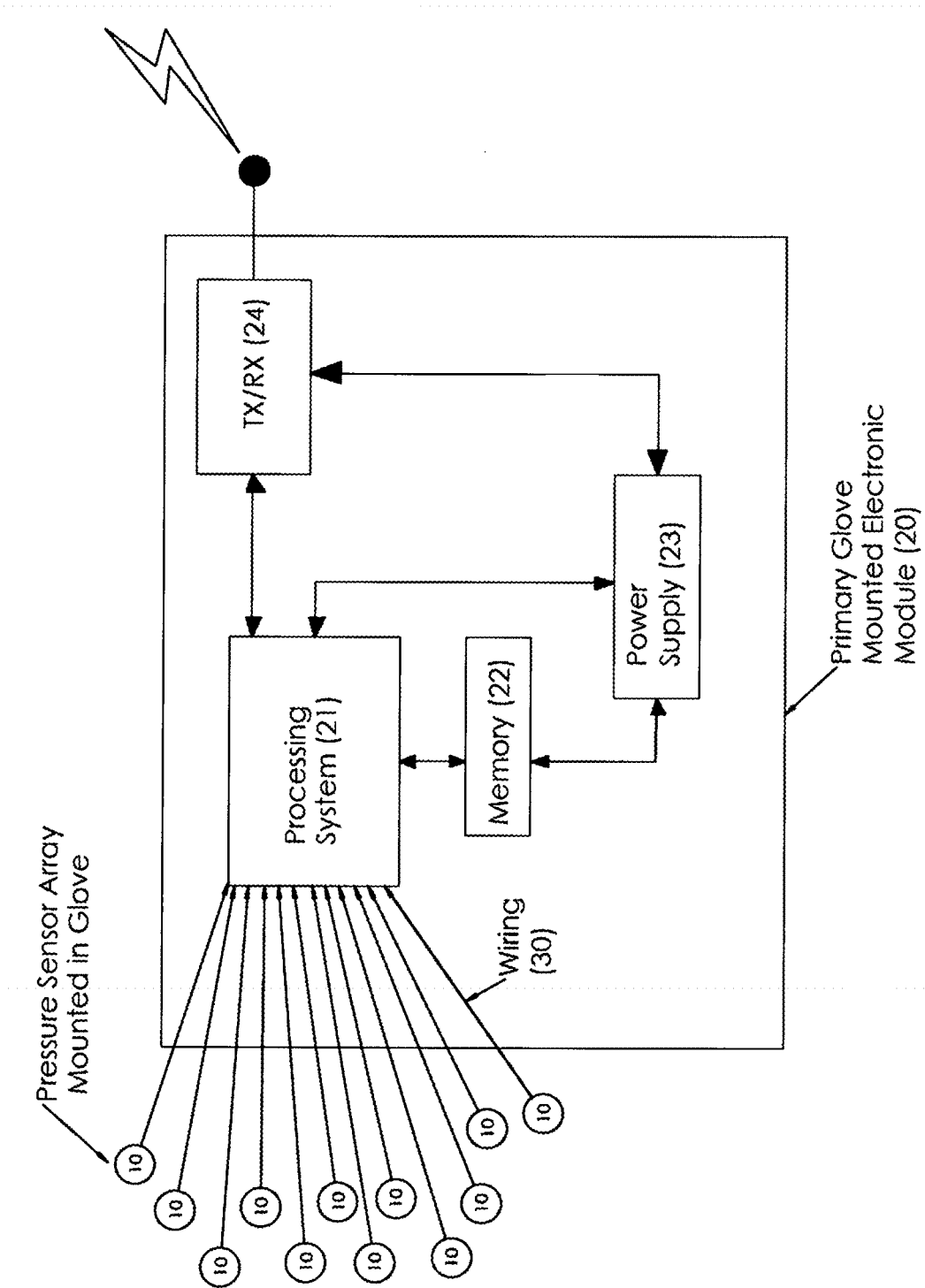
FIG. 6 is a schematic block diagram of the primary electronic module mounted in the glove.

Referring next to FIG. 6, the primary glove mounted electronic module 20 is shown. The module 20 contains various components that provide a means of sending pressure data measured from the gloves to a dedicated receiver contained in the secondary glove module 90. The components of the primary module 20 are: a processing system 21, a memory device 22, a power supply (battery) 23 and a transmitter/receiver unit 24. The processing system 21 is the main control unit for the module and provides several functions such as the conversion of voltage signals from the pressure sensor array 10 to a calculated average pressure value and the sending of the calculated pressure value to an RF transmitter 24. The processing system 21 stores the pressure data in memory device 22 until it is transmitted. By using a wireless enabled device with an app designed for use with this invention, a user can adjust how often the pressure data is transmitted. This feature will naturally extend the battery life if the transmitter rate is slowed down. The processing system 21 also continuously monitors the amount of pressure detected from any pressure sensor 10 in the glove and will automatically power off the module 20 after a preset time of no activity from the sensors has been reached in order to conserve battery life. The embedded power supply 23 is preferably a battery and provides electrical power to all components. The transmitter/receiver unit 24 transmits pressure data based on a frequency that is user selectable and stored in memory. Because the wearer of the glove may want different sensors to be activated based on exercise needs (for example weight lifting versus gripping a tennis racket), the pressure signals from each sensor 10 in the array may be individually set to "on" or "off" using a wireless enabled device and app. These settings are then stored in the memory 22 and used to calculate the average pressure of the selected sensors in the array. This method gives the user great flexibility in how the glove pressures are measured and what data is transmitted.

Figure 7:
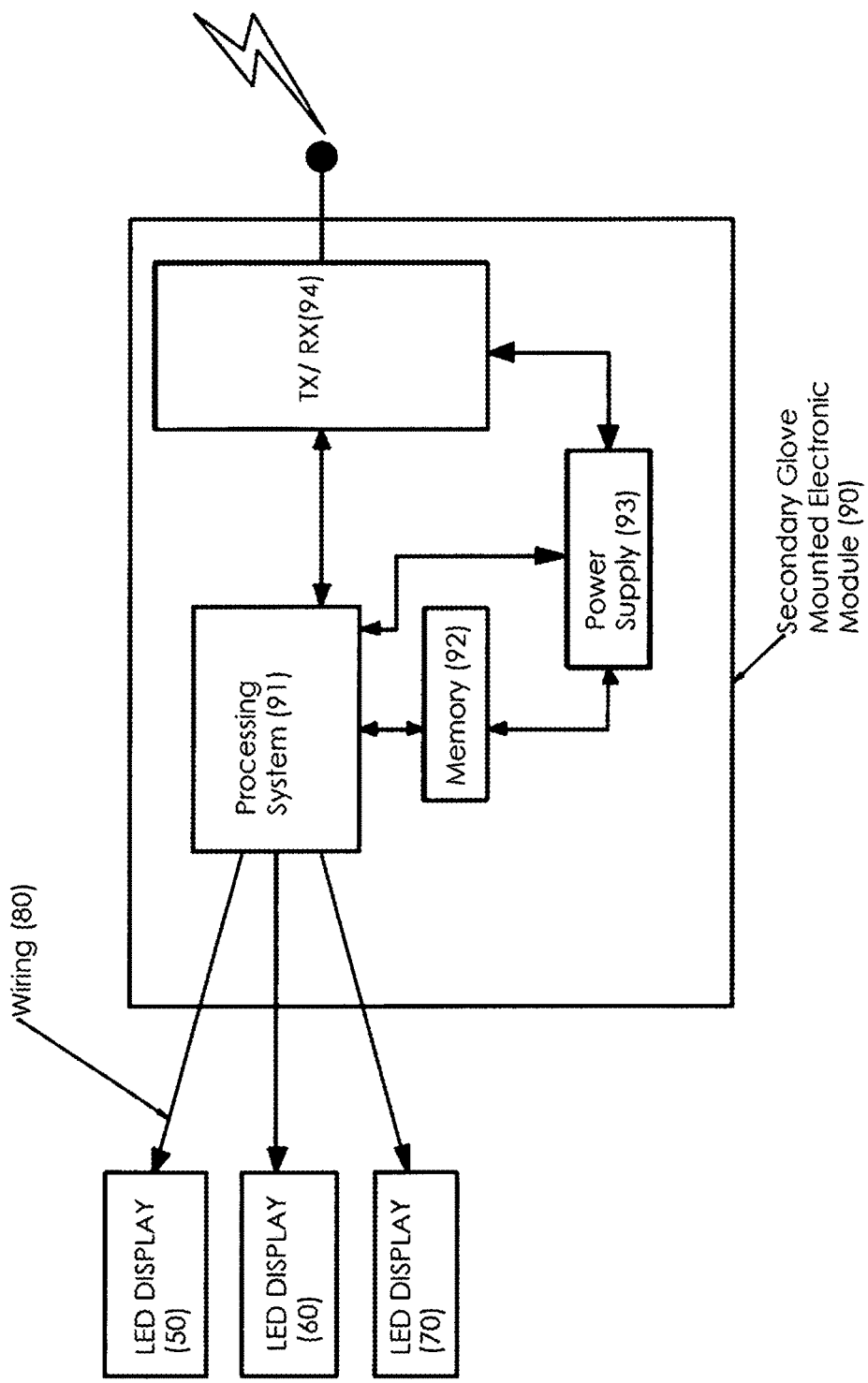
FIG. 7 is a schematic block diagram of the secondary electronic module mounted in the glove.

Referring next to FIG. 7, the glove mounted secondary electronic module 90 is shown. The module 90 contains various components that provide a means of displaying monitored glove and shoe pressure data performance in real time. Rather than display numerical values of pressure which could be both time consuming and distracting for the athlete to monitor, the preferred embodiment indicates performance based a simple display of colors using three LED displays 50, 60, and 70. The specific colors used are user selectable and programmed during setup of the apparatus using a wireless enabled device and dedicated app. The components of the secondary glove electronic module 90 are: a processing system 91, a memory device 92, a power supply 93 and a transmitter/receiver unit 94. The processing system 91 is the main control unit for the module and provides several functions such as the determination of color based performance conditions of the gloves and shoes and the sending of color command signals to the three LED displays 50, 60 and 70. By using a wireless enabled device with an app designed for use with this invention, a user can adjust several exercise settings such as (1) the specific colors for indicating in balance and out of balance pressures for the gloves and shoes; (2) the flashing display of either maximum or minimum pressure for the side that is unbalanced; (3) the refresh rate of the color displays; (4) what percentage of pressure difference is considered to be out of balance (5%, 10% etc.); and (5) the brightness level of the LED displays. The processing system 91 also continuously monitors the receiver 94 for the presence of any pressure data from either the glove or shoe modules and will automatically power off the module 90 after a preset time of no activity from the glove or shoe modules has been reached in order to conserve battery life. An embedded power supply 93 provides electrical power to all components and is preferably a battery. The transmitter/receiver unit 94 runs in receive mode when receiving pressure data transmitted from the glove and shoe electronic modules 20 and 210. The transmitter/receiver runs in transmit mode only to send "ping" signals to the modules 20 and 210 to trigger them to transmit. This is required for the processing system to organize the data and ensure the correct glove or shoe data is properly stored.

Figure 8:
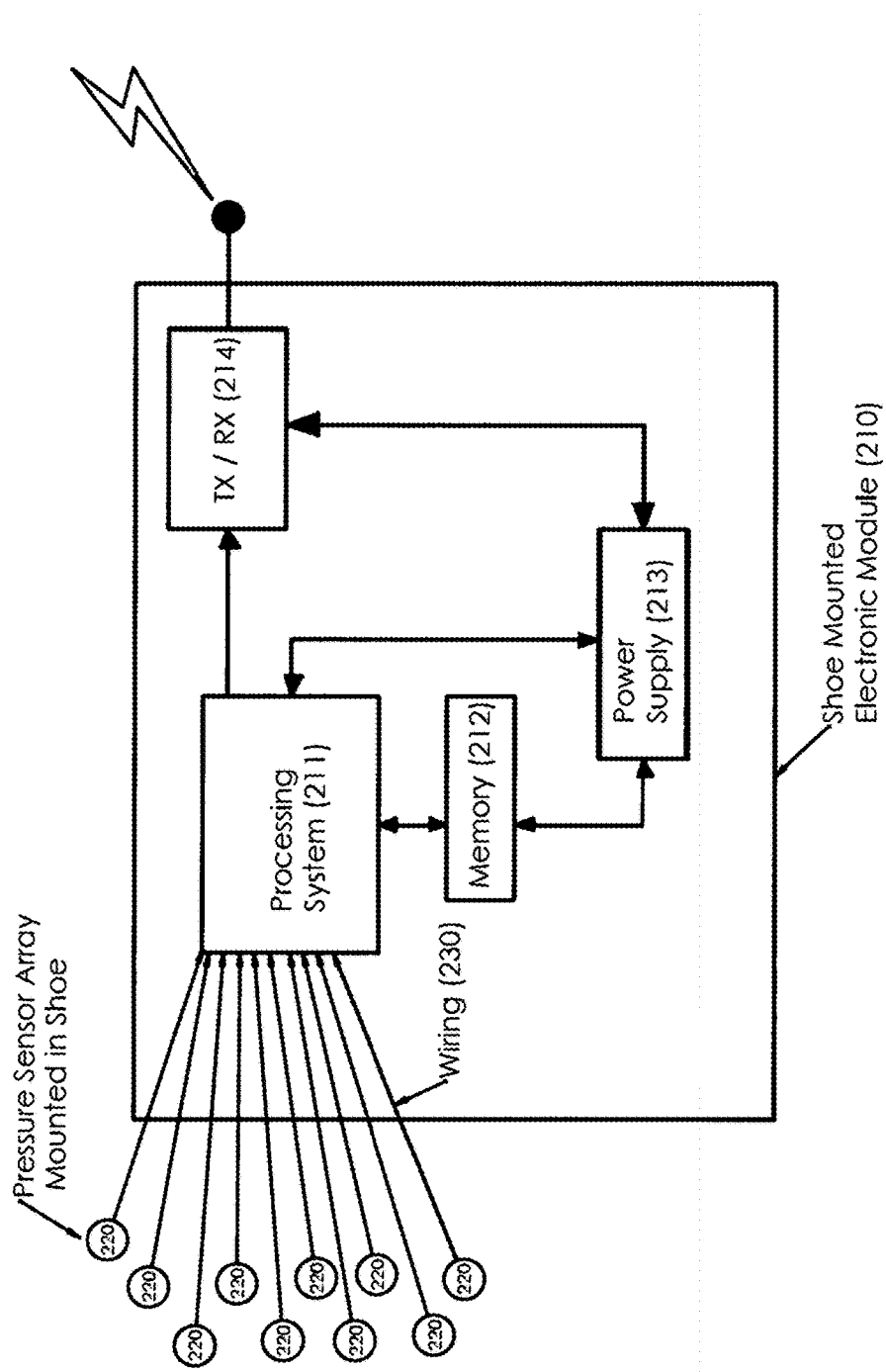
FIG. 8 is a schematic block diagram of the shoe electronic module.

Referring next to FIG. 8, the shoe mounted electronic module 210 is shown. The module 210 contains various components that provide a means of sending pressure data measured from the shoes to a dedicated receiver 94 contained in the secondary glove module 90. The components of the shoe electronic module 210 are: a processing system 211, a memory device 212, a power supply (battery) 213 and a transmitter/receiver unit 214. The processing system 211 is the main control unit for the module and provides several functions such as the conversion of voltage signals from the pressure sensor array 220 to a calculated average pressure value and the sending of the calculated pressure value to an RF transmitter 214. The processing system 211 stores the pressure data in memory device 212 until it is transmitted. By using a Wireless enabled device with an app designed for use with this invention, a user can adjust how often the pressure data is transmitted. The processing system 211 also continuously monitors the amount of pressure detected from any pressure sensor 220 in the shoe and will automatically power off the module 210 after a preset time of no activity from the sensors has been reached in order to conserve battery life. An embedded power supply 213 provides electrical power to all components. The transmitter/receiver unit 214 transmits pressure data based on a frequency that is user selectable and stored in memory. Because the wearer of the shoe may want different sensors to be activated based on exercise needs (for example running versus playing basketball), the pressure signals from each sensor 220 in the array may be individually set to "on" or "off" using a Wireless enabled device and app. These settings are then stored in the memory 212 and used to calculate the average pressure of the selected sensors in the array. This method gives the user great flexibility in how the shoe pressures are measured and what data is transmitted.

Figure 9:
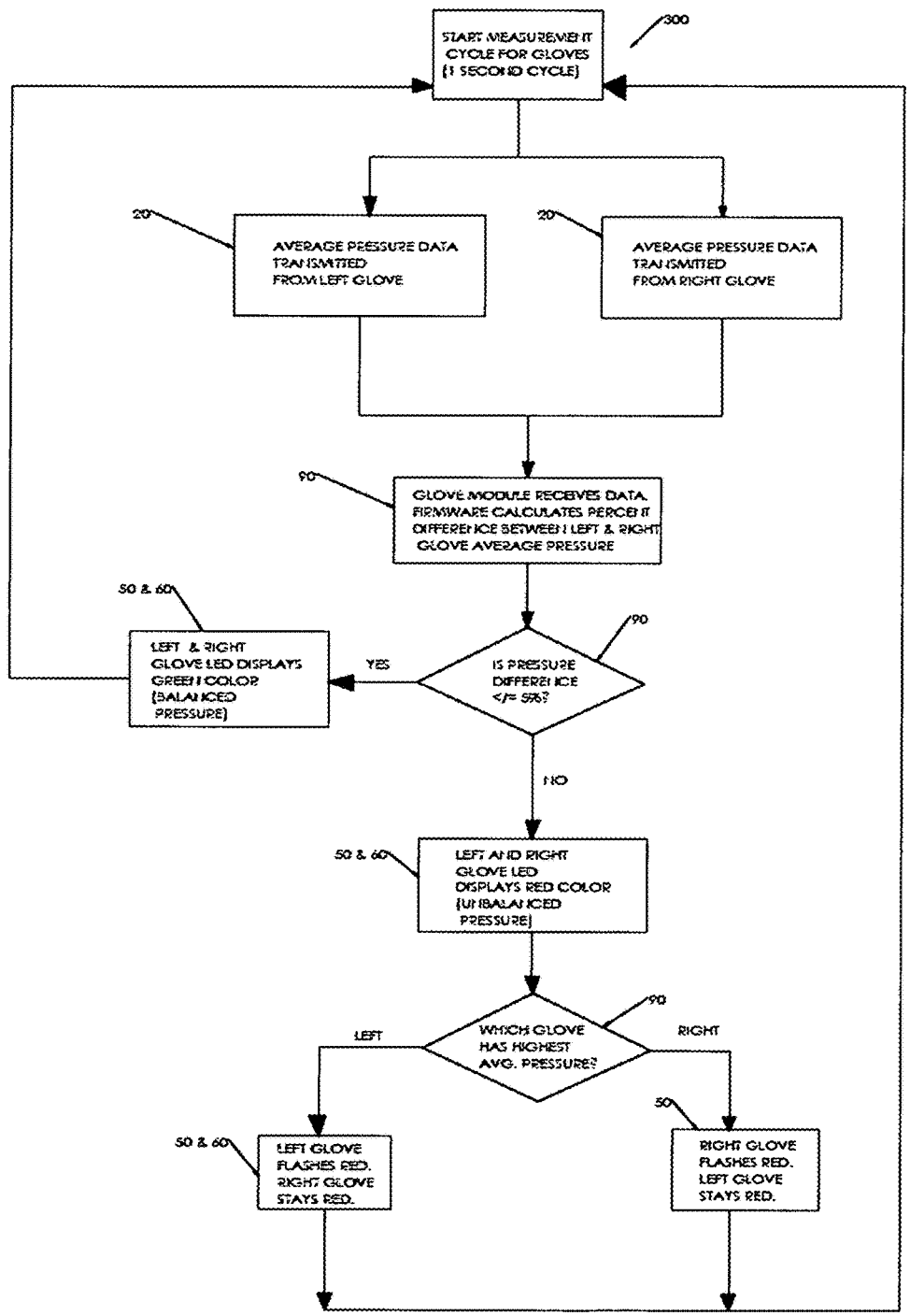
FIG. 9 illustrates an example exercise performance monitoring algorithm using pressure feedback from the pressure monitoring gloves.
Figure 10:
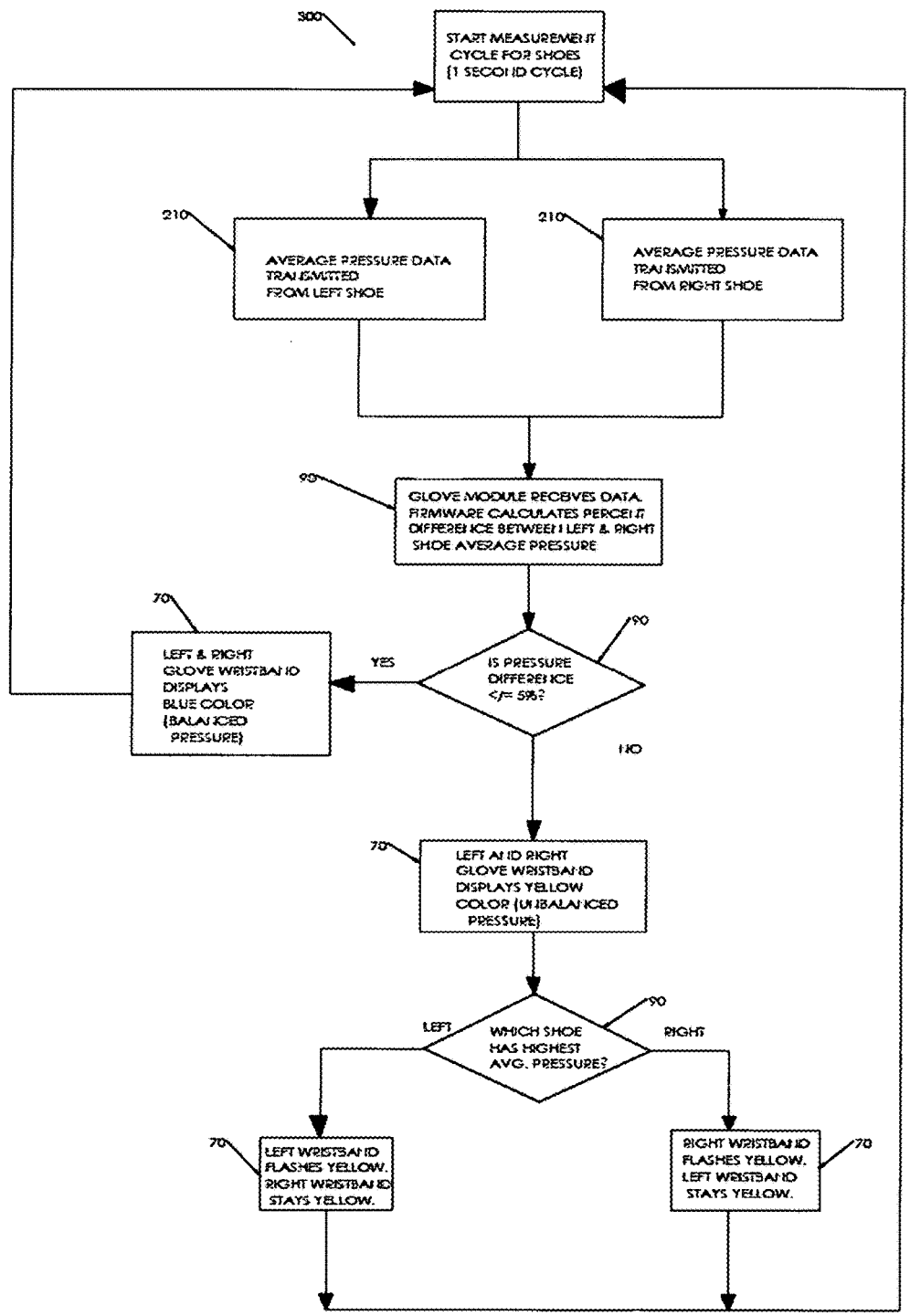
FIG. 10 illustrates an example exercise performance monitoring algorithm using pressure feedback from the pressure monitoring shoes.

Referring finally to FIGS. 9 & 10, an example exercise performance monitoring algorithm 300 of the preferred embodiment is shown. In the example shown, the user selected the following color combinations and settings:

RED=Glove pressures not balanced
GREEN=Glove pressures are balanced
FLASHING RED=Glove having the higher average pressure (not balanced)
YELLOW=Shoe pressures not balanced
BLUE=Shoe pressures are balanced
FLASHING YELLOW=Shoe having the higher average pressure (not balanced)
Balance set point=5% (example left glove pressure=10 psi, right glove must read between 9.5-10.5 psi to be in balance)
Pressure sensing rate=60 Hz (1 pressure reading transmitted per second)

The algorithm 300 requires settings to be transmitted by the user preferably through a wireless enabled device and a dedicated app. Although the details of the app software are not disclosed in this specification, one skilled in the art of developing app software could develop a program that communicates to the processing system 91 via the receiving unit 94 which would be designed to receive the wireless data from the device app. The user selectable settings for colors, balance set point, and pressure sensing rate are required for the algorithm 300 to perform the exercise monitoring. In the preferred embodiment, various versions of pressure measuring gloves 100 and shoes 200 would be provided for various sports such as weight lifting, yoga, gymnastics or body weight exercises. The sport played would therefore influence the pattern of and number of sensors to be embedded into the gloves. Various versions of pressure measuring shoes 200 can be provided for various sports such as weight lifting, yoga, gymnastics or body weight exercises.

The smart app could have these sports styles programmed as selections which would then determine the number and pattern of pressure sensors to be monitored by communicating with the glove and shoe modules 20 and 210.

Periodic updates to the algorithm 300 such as new performance monitoring algorithms for specific sports or changes to accommodate new glove designs with different LED display configurations than the preferred embodiment could be updated using the wireless enabled device app as the preferred method. It should be noted that alternative exercise performance monitoring algorithms in addition to the disclosed algorithm 300 are possible as new sports applications are identified and that the invention is intended to be used across many exercises and sports. By using a wireless enabled device and app software, these new algorithms will become available as new sport specific applications are developed.

As an alternative embodiment to using the LED displays of the pressure sensing gloves 100 to display the exercise performance results, a wireless enabled device such as a smart phone may also be used to display these results for either the gloves and/or shoes. This allows the user to monitor his or her exercise results without the need to also purchase the pressure sensing gloves 100. The wireless enabled device can be set by the user to display either just the glove or shoe pressures or both glove and shoe pressures. In the case where the wireless enabled device is also being used to display the glove pressures, the LED displays of the pressure sensing gloves 100 can be powered off to conserve the battery life.

What is claimed is:

1. An apparatus for exercise performance monitoring comprising:
   a pair of pressure sensing shoes, comprising a first shoe and a second shoe, wherein
      the first shoe has a first plurality of embedded pressure sensors wired to a first embedded shoe mounted electronic module; and
      the second shoe has a second plurality of embedded pressure sensors wired to a second embedded shoe mounted electronic module;
   a pair of pressure sensing gloves, comprising a first glove and a second glove;
      wherein the first glove has a third plurality of embedded pressure sensors wired to a first primary embedded electronic module, and a first plurality of embedded color LED displays, wherein each LED display is wired to a first secondary embedded electronic module, and
      the second glove has a fourth plurality of embedded pressure sensors wired to a second primary embedded electronic module, and a second plurality of embedded color LED displays, wherein each of the second plurality of LED displays is wired to a second secondary embedded electronic module;
   wherein the first, secondary embedded electronic module includes a first processor and a first memory storing a first computer algorithm with instructions for the first processor to convert pressure data input received from said first and second pressure sensing gloves and said first and second pressure sensing shoes into a real time exercise performance monitoring output thereby controlling the first and second plurality of embedded color LED displays to display solid or flashing colors configured to communicate a state of pressure balance or imbalance; and
   wherein the second, secondary embedded electronic module includes a second processor and a second memory storing a second computer algorithm with instructions for the second processor to convert pressure data input received from said first and second pressure sensing gloves and said first and second pressure sensing shoes into a real time exercise performance monitoring output thereby controlling the first and second plurality of embedded color LED displays to display solid or flashing colors configured to communicate a state of pressure balance or imbalance.

2. The apparatus of claim 1, wherein each of the first and second shoes further comprise:
   connecting wiring between one of a respective said first and second plurality of pressure sensors and a respective one of said first and second embedded shoe mounted electronic modules, wherein
   the respective first and second plurality of pressure sensors are embedded into a respective insole of the first and second shoes.

3. The apparatus of claim 1 wherein each of the first and second embedded shoe mounted electronic module comprises:
   a printed circuit board comprising a processor, a memory, a power supply, a transmitter/receiver; and
   a housing to protect the printed circuit board.

4. The apparatus of claim 3 wherein the processor, in said first and second embedded shoe mounted electronic modules, further comprises:
   a plurality of traces connecting to a respective one of said first and second plurality of embedded pressure sensors; and
   separate connections to:
      a respective one of said memories of said first and second embedded shoe mounted electronic modules;
      a respective one of said power supplies of said first and second embedded shoe mounted electronic modules; and
      a respective one of said first and second transmitter/receivers of said first and second embedded shoe mounted electronic modules.

5. The apparatus of claim 1 wherein each of the first and second embedded shoe mounted electronic modules include a receiver configured to update a performance monitoring algorithm by receiving commands via a control application from a wireless enabled device.

6. The apparatus of claim 3 wherein each of the first and second embedded shoe mounted electronic modules include a transmitter configured to transmit an average pressure value calculated from a respective one of said first and second processors to a receiver located in a respective one of the first and second primary embedded mounted electronic modules.

7. The apparatus of claim 1 wherein the third and fourth plurality of embedded pressure sensors are embedded into an interior of a glove housing fabric of a respective one of the first and second gloves wherein the first and second gloves each further include connecting wiring between a respective one of the third and fourth plurality of embedded pressure sensors and a respective one of said first and second primary embedded electronic modules.

8. The apparatus of claim 1 wherein each of said first and second gloves comprise two separate color LED displays configured to display exercise output results for glove pressures and are embedded into an exterior of a respective glove housing fabric of each of the first and second gloves wherein, on each of the first and second gloves, a first of the LED displays is located adjacent to the knuckles of the respective glove on a side opposite of a palm side of the glove and a second of the LED displays is located on a thumb finger of the respective glove on the palm side of the glove.

9. The apparatus of claim 8 wherein each of said first and second gloves contain a third color LED display configured to display exercise output results for respective shoe pressures, said third color LED display being located at a wrist end of the respective glove; said third color LED display wrapping a full 360 degrees around an exterior of a housing of the respective glove.

10. The apparatus of claim 9 wherein each of the first and second primary embedded electronic modules comprise:

a printed circuit board including a processor, a memory, a power supply, a transmitter/receiver; and a housing to protect the printed circuit board.

11. The apparatus of claim 10 wherein the processor, in each of the first and second primary embedded electronic modules, further comprises:

a plurality of traces connecting to a respective one of the third and fourth plurality of embedded pressure sensors; and separate connections to:

said memory of a respective one of the first and second primary embedded electronic modules;

said power supply of a respective one of the first and second primary embedded electronic modules; and said transmitter/receiver of a respective one of the first and second primary embedded electronic modules.

12. The apparatus of claim 10 wherein, in each of the first and second gloves, the respective transmitter/receiver of said respective primary glove electronic module is configured to update a performance monitoring algorithm by receiving commands via a control application from a wireless enabled device.

13. The apparatus of claim 10 wherein, in each of the first and second gloves, the respective transmitter/receiver of said respective primary embedded electronic module is configured to transmit an average pressure value calculated from said respective processor to the receiver located in the secondary embedded electronic module.

14. The apparatus of claim 11 wherein each of the first and second secondary embedded electronic modules comprises:

a printed circuit board including:

a respective one of said processors of said first or second secondary embedded electronic modules;

a respective one of said memories of said first or second secondary embedded electronic modules;

a power supply; and a transmitter/receiver; and a housing to protect the printed circuit board.

15. The apparatus of claim 14 wherein the processor, in each of the first and second gloves, further comprises:

a trace connecting to each one of the three color LED displays in a respective one of the first and second gloves; and separate connections to:

said memory of said respective embedded electronic modules;

said power supply of a respective one of the first and second primary embedded electronic modules; and said transmitter/receiver of a respective one of the first and second primary embedded electronic modules.

16. The apparatus of claim 14 wherein the transmitter/receiver in each of said secondary embedded electronic modules is configured to update a performance monitoring algorithm by receiving commands via a control application from a wireless enabled device.

17. The apparatus of claim 14 wherein the transmitter/receiver in each of said secondary embedded electronic modules is configured to transmit control signals to a respective one of said primary embedded electronic modules and a respective one of said embedded shoe mounted electronic modules for adjusting a rate of pressure data that the respective primary embedded electronic module sends out to the respective secondary embedded electronic module.

18. The apparatus of claim 14 wherein, in each of the first and second gloves, the exercise output results displayed by said LED displays embedded in the gloves is configured to be adjusted by sending commands to said respective secondary embedded electronic module using a control application from a wireless enabled device.

19. The apparatus of claim 14 wherein, a number of active shoe embedded pressure sensors of a respective one of the first or second plurality of embedded pressure sensors to be used for an exercise, is configured to be adjusted by sending commands to a respective one of said first or second secondary embedded electronic modules using a control application from a wireless enabled device; and a number of active glove embedded pressure sensors of a respective one of the third or fourth plurality of embedded pressure sensors to be used for an exercise, is configured to be adjusted by sending commands to a respective one of said first or second secondary embedded electronic modules using said control application from said wireless enabled device.

20. The apparatus of claim 14 wherein, in each of the first and second gloves, a wireless enabled device using a control application is capable of sending commands to a respective one of the first and second secondary embedded electronic modules for displaying different colors in the flashing display of the respective color LED displays, based on pressure imbalances, to either show minimum or maximum pressure.

21. The apparatus of claim 1 wherein, in each of the first and second gloves, a percentage of pressure difference between the first and second gloves or the first and second shoes, that is considered to be in balance, may be adjusted to a specific percentage value for both glove and shoe pressures by sending commands to a respective one of said first and second secondary embedded electronic modules using a control application from a wireless enabled device.

22. The apparatus of claim 1 wherein a wireless enabled device such as smart phone may be used as an alternative means to the LED displays, to display the exercise performance output of either said first and second gloves or said first and second shoes or both first and second gloves and both first and second shoes depending on a user preference.

* * * * *